(12) United States Patent
Kröning et al.

(10) Patent No.: US 8,109,147 B2
(45) Date of Patent: Feb. 7, 2012

(54) METHOD AND DEVICE FOR AN IMAGING ULTRASONIC INSPECTION OF A THREE-DIMENSIONAL WORKPIECE

(75) Inventors: Michael Kröning, Saarbrücken (DE); Andrey Bulavinov, Saarbrücken (DE); Krishna Mohan Reddy, Saarbrücken (DE); Ludwig Von Bernus, Windsbach (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 318 days.

(21) Appl. No.: 12/091,801

(22) PCT Filed: Sep. 29, 2006

(86) PCT No.: PCT/EP2006/009484
§ 371 (c)(1),
(2), (4) Date: Nov. 2, 2009

(87) PCT Pub. No.: WO2007/048479
PCT Pub. Date: May 3, 2007

(65) Prior Publication Data
US 2010/0064811 A1   Mar. 18, 2010

(30) Foreign Application Priority Data
Oct. 28, 2005   (DE) .......................... 10 2005 051 783

(51) Int. Cl.
G01N 29/04   (2006.01)
A61B 8/14   (2006.01)

(52) U.S. Cl. ................ 73/628; 73/597; 73/598; 73/602; 600/443; 600/447

(58) Field of Classification Search .................... 73/628, 73/597, 598, 599, 600, 602; 600/443, 447
See application file for complete search history.

(56) References Cited

U.S. PATENT DOCUMENTS

| | | | |
|---|---|---|---|
| 5,465,722 A | 11/1995 | Fort et al. | |
| 5,842,473 A * | 12/1998 | Fenster et al. | 600/445 |
| 5,964,707 A * | 10/1999 | Fenster et al. | 600/443 |
| 6,048,312 A * | 4/2000 | Ishrak et al. | 600/443 |
| 6,102,861 A * | 8/2000 | Avila et al. | 600/443 |
| 6,126,603 A * | 10/2000 | Hatfield et al. | 600/454 |
| 6,238,346 B1 | 5/2001 | Mason | |
| 6,347,551 B1 | 2/2002 | Turpening et al. | |
| 6,461,298 B1 * | 10/2002 | Fenster et al. | 600/437 |
| 6,878,115 B2 | 4/2005 | Dione et al. | |
| 2003/0177833 A1 | 9/2003 | Venczel | |

FOREIGN PATENT DOCUMENTS

| | | |
|---|---|---|
| AU | 1 811 873 | 7/1969 |
| DE | 102 48 979 A1 | 4/2003 |
| WO | WO 2004/005957 A1 | 1/2004 |

* cited by examiner

*Primary Examiner* — J M Saint Surin
(74) *Attorney, Agent, or Firm* — Antonelli, Terry, Stout & Kraus, LLP.

(57) ABSTRACT

A method for an imaging ultrasonic inspection of a three-dimensional workpiece, in which ultrasonic waves are coupled into the workpiece with at least one ultrasonic transducer and ultrasonic waves reflected within the workpiece are received by ultrasonic transducers and converted into ultrasonic signals forming the basis of the non-destructive imaging ultrasonic inspection.

26 Claims, 1 Drawing Sheet

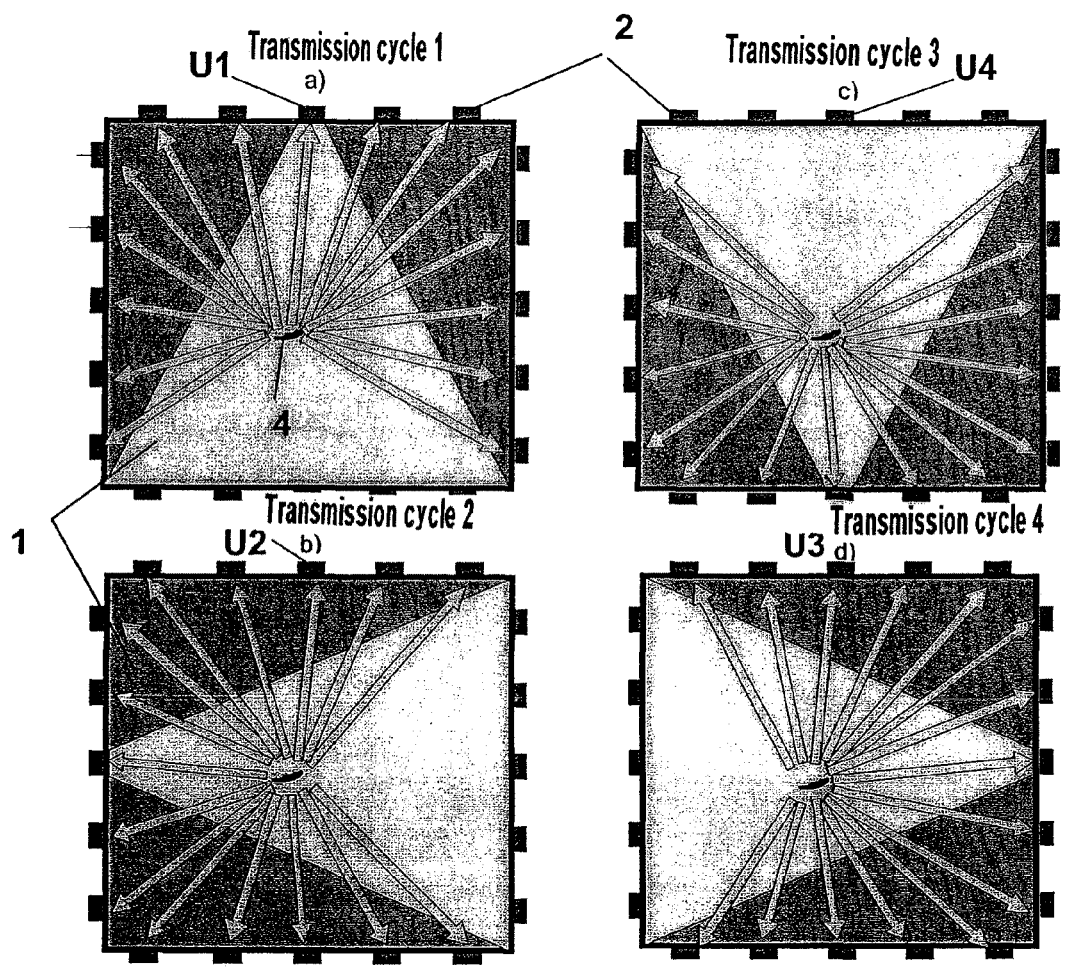
Fig. 1 a)-d)
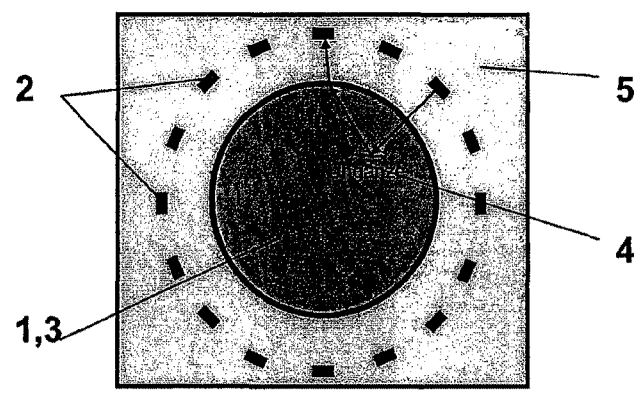
Fig. 2

METHOD AND DEVICE FOR AN IMAGING ULTRASONIC INSPECTION OF A THREE-DIMENSIONAL WORKPIECE

BACKGROUND OF THE INVENTION

1. Field of the Invention

The invention pertains to a method for an imaging ultrasonic inspection of a three-dimensional workpiece, in which ultrasonic waves are coupled into the workpiece with one ultrasonic transducer or a number of ultrasonic transducers and ultrasonic waves reflected within the workpiece are received by a number of ultrasonic transducers and converted into ultrasonic signals forming the basis of the non-destructive imaging ultrasonic inspection.

2. Description of the Art

The non-destructive inspection of a test body by means of ultrasound, for example, for testing materials for material defects such as cracks, inclusions or other material nonhomogeneities comprises the coupling of ultrasonic waves into the test body, the detection of the ultrasonic waves that are transmitted through the test body or reflected, diffracted, scattered and/or refracted within the test body, as well as the evaluation of the ultrasonic waves that are converted into ultrasonic signals.

The above-described known inspection method makes it possible to determine and evaluate the ultrasonic transmission properties and reflection properties of a test body. In this method that was originally developed in medical engineering (ultrasound diagnostics), defective spots such as material cracks, foreign inclusions or material boundaries situated within a test body can be illustrated in the form of regions with different reflection properties by evaluating the received ultrasonic signals accordingly. The position, shape and size of the defective spots can be illustrated three-dimensionally with a high resolution.

It is quite obvious that this method is used in numerous fields of application. For example, this method is used for testing and measuring homogeneity or stability properties of structural components (concrete walls, ceiling or wall elements, etc.) or for detecting cracks, for example, in wheels of rail vehicles or aircraft parts.

A number of ultrasonic transducers that are combined into a so-called ultrasonic probe or array probe in order to simplify their handling are used in many instances of non-destructive material testing by means of ultrasound. There basically exist two types of ultrasonic probes. A pulse-echo probe is used if the probe couples an ultrasonic wave packet into the test body and then receives the ultrasonic waves reflected within the test body. Probes with separate ultrasonic transducers for coupling in and for receiving ultrasonic waves are referred to as transmitting-receiving probes.

In all ultrasonic test systems with sound field control known to date, the individual ultrasonic transducers are acted upon in a time-coordinated fashion such that the ultrasonic transducers can be activated independently of one another in a time-controlled fashion and, for example, serve as ultrasonic transmitters or receivers. Such a separate activation makes it possible, in particular, to respectively operate the individual ultrasonic transducers with different phase position and amplitude.

Array probes, in which a number of individual ultrasonic transducers are provided in order to realize a controlled emission and detection of ultrasonic waves, are able to stimulate ultrasonic waves in a test body under arbitrary acoustic irradiation angles and in any predefined focusing ranges and to receive ultrasonic waves from these acoustic irradiation regions. In order to carry out such a measurement for investigating the ultrasonic transmission capability of a test body, a control device acts upon at least one ultrasonic transducer of the array probe, usually several ultrasonic transducers of the array probe for a limited, brief time interval in order to couple ultrasonic waves into the test body. The thusly created ultrasonic wave packets being coupled in are reflected, for example, on material discontinuities within the test body and returned to the ultrasonic transducers that now operate as receivers in the form of reflected ultrasonic waves, wherein the ultrasonic transducers convert the reflected ultrasonic waves into ultrasonic signals and transmit these ultrasonic signals to the control device for evaluation purposes. The time period between the beginning of the transmission process and the end of the reception process of the ultrasonic signals is usually referred to as a measuring cycle.

In many instances, it is important to determine the transmission and reflection properties of a test body with the highest possible resolution within the test body volume. To this end, the time delays for the transmission cycles are adjusted accordingly in order to predefine the acoustic irradiation direction as well as the depth of field. The received ultrasonic signals of the individual ultrasonic transducers of the array probe are added up with corresponding phase delays such that an ultrasonic signal for a certain acoustic irradiations angle and, if applicable, a certain depth of field is generated in a transmission cycle, wherein such instances are referred to as so-called A-images. The A-image represents the ultrasonic echo along a predefined "viewing or sound propagation direction" through the test body. Such an image can be considered as a 1-dimensional sectional image similar to a line of section through the test body, along which ultrasonic echo signals are illustrated in a spatially resolved fashion. If the ultrasonic transmission through the test body takes place at different angles, that is if the sound beam is pivoted in the test body, preferably within a uniform pivoting plane, it is possible to reconstruct a so-called sector image that is composed of a number of individual A-images.

The disadvantages of utilizing the phased array method for a non-destructive material inspection on a test body, however, can be seen in the expenditure of time and the metrological expenditure until a test body is inspected in a largely complete fashion, namely because it is essential for a complete signal evaluation to obtain sufficiently reliable measuring signals from all regions of the test body volume. For example, only information on the reflection properties along a predefined acoustic irradiation direction of the test body can be obtained in one measuring cycle or a number of individual measuring cycles with identical phase control of the ultrasonic transducers. Consequently, an inspection of the entire test body volume requires a very large number of measurements with respectively different phase controls such that the expenditure of time for the complete material test is quite high. The adjustment of a new acoustic irradiation angle or a new focal position also requires a labor-intensive and time-consuming reprogramming process.

Another disadvantage can be seen in that a predefined acoustic irradiation angle specifies the probe aperture, that is, the aperture cannot be optimally chosen for all acoustic irradiation angles such that the resolution of the measurements deteriorates.

If controls with respect to the manufacturing quality of industrial products should be carried out online by means of currently available ultrasonic test techniques, that is, as an integral part of the manufacturing process, the measures required for the quality inspection should not have any effects that impede or slow down the manufacturing process. The manufacture of workpieces realized in the form of extruded profiles, for example, steel billets, rods or profiles of any type such as, in particular, rails manufactured in an extrusion moulding process requires reliably operating test methods in order to fulfill the strictest quality requirements. As initially mentioned, online inspections of workpieces in the form of extruded profiles that are transported or conveyed along production lines with speeds of a few meters per second by means of ultrasonic test techniques known so far are not sufficiently fast and associated with excessive costs and device expenditures. Even imaging reconstruction methods that are based on the so-called synthetic aperture technique (Synthetic Aperture Focusing Technique—SAFT), in which all ultrasonic signals received at different measuring points of the test object are projected back into the material, require a substantial expenditure of time for the measurement and the image reconstruction such that they are completely unsuitable for an online inspection. The reasons for this substantial expenditure of time can be seen in the recording of the ultrasonic signals with a moving ultrasonic transducer and the time-consuming evaluation of the recorded ultrasonic time signals for the image reconstruction.

Another disadvantage of thus far known ultrasonic test techniques that utilize array systems can be seen in the restricted mutual spacing between the ultrasonic transducers that should be smaller than half the wavelength of the ultrasonic waves to be coupled into the respective test body so as to prevent false echoes or artifacts in the reconstructed ultrasonic image.

SUMMARY OF THE INVENTION

The invention is a method for an imaging ultrasonic inspection of a three-dimensional workpiece, in which ultrasonic waves are coupled into the workpiece with one ultrasonic transducer or a number of ultrasonic transducers and ultrasonic waves reflected within the workpiece are received by a number of ultrasonic transducers and converted into ultrasonic signals forming the basis of the non-destructive imaging ultrasonic inspection, namely such that it is possible to realize a fast and online-compatible inspection of workpieces that preferably should be carried out during their manufacturing process. The required expenditures with respect to devices, evaluation technology and ultimately costs should be maintained as low as possible and costly and bulky sensor carriers should be largely eliminated. Furthermore, it should be possible to carry out the inventive method independently of the manner in which the ultrasonic waves are coupled into the test body.

The invention is based on a novel metrological approach in connection with algorithms for reconstructing ultrasonic images while simultaneously suppressing artifacts at imperfect apertures in the physical-mechanical sense.

The method therefore comprises the following steps: n ultrasonic transducers are arranged around a workpiece to be inspected which is realized in the form of an extruded profile or rod, for example, a rail track, in a cross-sectional plane of the workpiece, preferably along a line. The ultrasonic transducers preferably are arranged around the workpiece in a uniformly distributed fashion, that is, with a respectively identical spacing between two directly adjacent ultrasonic transducers referred to the circumferential direction. In such a measuring constellation, a first ultrasonic transducer or the first group i of ultrasonic transducers that are preferably arranged adjacent to one another is activated in order to realize the acoustic irradiation of a first ultrasonic field or of i ultrasonic fields into the workpiece. When activating a group i of ultrasonic transducers, the number i needs to be chosen smaller than the number of all ultrasonic transducers arranged around the workpiece.

In contrast to the generation of ultrasonic waves, a number m of ultrasonic transducers, preferably the entire number n of ultrasonic transducers that are three-dimensionally distributed around the workpiece, is available for receiving the ultrasonic waves that are reflected within the workpiece or transmitted through the workpiece. This means that the ultrasonic waves coupled into the workpiece by at least one ultrasonic transducer are received by a number of ultrasonic transducers, preferably by all ultrasonic transducers arranged around the workpiece. The ultrasonic time signals that are detected by the ultrasonic transducers and contain amplitude information in a temporally resolved fashion are correspondingly stored for subsequent reconstructive processing or immediately fed to an evaluation, in which a 2-dimensional ultrasonic image, that is, a B-image, is reconstructed or an A-image in the form of a one-dimensional ultrasonic echo signal is reconstructed along a predefined acoustic irradiation angle in a temporally and spatially resolved fashion, namely by utilizing the stored or prepared ultrasonic signals only.

Since the reception apertures of the ultrasonic transducers arranged around the workpiece overlap, namely at least the reception apertures of two ultrasonic transducers that are arranged directly adjacent to one another, the central region of the workpiece volume can be surveyed in its entirety. This is referred to as a so-called closed aperture which ensures that all ultrasonic waves emerging from the workpiece can be detected from different directions in space after being reflected on material discontinuities in the workpiece or after being transmitted through the workpiece in an unhindered fashion.

It would be possible, in principle, to obtain sufficient information for generating a B-image or an A-image from the ultrasonic echoes detected during the course of a single measuring cycle, that is, during a single activation of an ultrasonic transducer or a group i of ultrasonic transducers and the reception of the ultrasonic echoes. Depending on the type of workpiece to be inspected, the defined measuring task and the required recording quality and image resolution, it is advantageous to acoustically irradiate the workpiece from different directions in space in several measuring cycles, namely with differently positioned ultrasonic transducers or differently positioned groups i of ultrasonic transducers. However, all ultrasonic transducers grouped around the workpiece preferably serve as receivers in each measuring cycle. Due to this measure, possible material discontinuities within the workpiece are acoustically irradiated in a cyclic fashion with ultrasonic fields from different directions in space, wherein the respectively reflected ultrasonic waves are detected and correspondingly stored by all ultrasonic transducers, namely with consideration of the respective ultrasonic transit times and amplitude information. Based on the stored ultrasonic transit time signals, B-images for the respective test position of the workpiece to be inspected relative to the ultrasonic wave arrangement are reconstructed with the aid of special reconstruction modules and reconstruction techniques. The main aspect forming the basis of the reconstruction therefore takes into account the ultrasonic transit times from each individual ultrasonic transmitter to a certain point in space within the workpiece to be inspected and back to each individual ultrasonic receiver. Such a transit time-related reconstruction makes it possible to divide the volume of the workpiece to be inspected into a multitude of individual small volume regions or so-called voxels, to which ultrasonic echo signals are respectively assigned in dependence on amplitude information and transit time information. In this respect, the transit time-related reconstruction results in a focusing effect, wherein the focal point lies in each individual voxel of the workpiece volume to be inspected. Due to the uniform spatial distribution of all ultrasonic transducers provided for the transmission and the reception of ultrasonic waves along a linear arrangement around the workpiece to be inspected, the multitude of individual voxels, to which corresponding ultrasonic transit time signals can be assigned, preferably lies in a two-dimensional plane of section through the workpiece. Due to the directness of the ultrasonic time signals detected by the ultrasonic transducers as well as the fast assignment of individual time and amplitude information to the individual voxels by means of corresponding evaluation technology, it is possible to obtain a sector image or B-image through the workpiece online. In this case, the ultrasonic information that can be assigned to the individual voxels is illustrated on an image plane that represents the acoustically irradiated plane of section through the workpiece, for example, by means of numerical data or color coding, such that it is also possible to visually evaluate the ultrasonic signals obtained online.

An improved sectional image or a material discontinuity that is acoustically irradiated from all sides in space is respectively realized by carrying out a number of individual measuring cycles in rapid succession, wherein all ultrasonic transmitters distributed around the workpiece respectively serve as transmitters. The sectional images or A-images obtained in each individual measuring cycle are combined in order to thusly obtain a largely complete view of possible material discontinuities within the workpiece.

The high measuring and evaluation speeds achieved with the invention also make it possible to acoustically irradiate workpieces that move along a production line with transport speeds of a few m/sec, for example, up to 10 m/sec, in the above-described measuring mode, that is, the workpieces are acoustically irradiated by all ultrasonic transducers in individual successive measuring cycles in order to obtain meaningful sectional images that form the basis for evaluating the workpiece quality.

If several sectional images are produced sequentially due to the self-movement of the workpiece to be inspected, the combination of a multitude of individual sectional images recorded in the longitudinal direction of a workpiece makes it possible to realize a 3D reconstruction of the complete workpiece by means of a corresponding interpolation between the individual B-images.

The method of the invention is described in greater detail below with reference to concrete embodiments.

BRIEF DESCRIPTION OF THE DRAWINGS

The invention is described in an exemplary fashion below with reference to embodiments that are illustrated in the figures, namely without restricting the general object of the invention. The figures show:

FIGS. 1a to d are illustrations of sequential images for carrying out four successive measuring cycles, and FIG. 2 is a schematic representation of an ultrasonic transducer arrangement within a water bath.

DESCRIPTION OF THE INVENTION

With respect to a pictorial explanation of the invention, reference is made to the transmission cycles 1 to 4 according to the illustrations shown in FIGS. 1a to d. It is assumed that the ultrasonic transducers 2 uniformly distributed around the lateral edges of an oblong workpiece 1 are in the form of an array system, that is, the number of individual ultrasonic transducers can be individually activated in a time-delayed fashion as required for the transmission and reception mode according to the Sampling Phased-Array technique. The longitudinal direction of the workpiece 1 is, for example, in the form of an extruded steel profile with square cross section is oriented perpendicular to the plane of projection of FIG. 1.

In a first transmission cycle that is illustrated in FIG. 1a, a first ultrasonic transducer U1 is activated, wherein the transmission aperture of the ultrasonic transducer has a shape that diverges in a cone-shaped fashion. The ultrasonic waves reflected on the material discontinuity 4 in the interior of the workpiece 1 are received by all ultrasonic transducers 2 arranged around the workpiece 1. In an ensuing transmission cycle 2, an ultrasonic transducer U2 is activated which is offset by 90°, wherein the reflection signals are also received by all remaining ultrasonic transducers 2. This applies analogously to the following transmission cycles 3 and 4, in which individual ultrasonic transducers U3, U4 that are respectively offset by 90° are activated accordingly. After the four transmission cycles illustrated in FIGS. 1a to d, the material discontinuity 4 in the interior of the workpiece 1 is acoustically irradiated from all directions in space such that the shape and the size of the material discontinuity can be exactly determined by combining and evaluating the sequential ultrasonic images. However, it is imperative that the inventive arrangement of the ultrasonic transducers relative to the workpiece 1 and their corresponding cyclic activation ensure a 100% coverage of the internal test region 3 within the workpiece 1, wherein material discontinuities within the workpiece can be detected with arbitrary orientation.

The number and the size of the ultrasonic transducers to be provided along the workpiece to be inspected results from the respectively required defect detection limits and the spatial geometry of the workpiece to be inspected. It is also possible to utilize the method of the invention in connection with suitable coupling mediums between the individual ultrasonic transducers and the workpiece to be inspected, for example, within a water bath 5 illustrated in FIG. 2. In this case, the individual ultrasonic transducers 2 are circularly arranged around a workpiece 1 of circular cross section, that is, circularly spaced apart from one another. The ultrasonic transducers as well as the workpiece 1 are situated in a water bath 5 in order to couple in the sound.

In comparison with conventional techniques for coupling in ultrasonic waves, the method of the invention provides the following advantages:

The phased array principle makes it possible to reconstruct the complete B-image at the respective test position. In this case, a 100% coverage of the entire test volume can be achieved.

The detection of arbitrarily oriented material discontinuities is ensured while the aperture of the phased array is closed.

Special reconstruction algorithms make possible achieving a reconstruction in real time and a quantitative evaluation of 2D-images at test speeds of the moving test object up to a few meters per second.

The automatic focusing in each point of the ultrasonic image improves the test engineering characteristics such as the test sensibility and the resolution.

Due to the utilization of synthetic focusing, the main lobes of higher order in the directional characteristic of the array are suppressed at a large element spacing ($>\lambda/2$). This makes it possible to realize a quasi closed aperture with a small number of array elements.

An optimized probe arrangement makes it possible to achieve the required test sensibility for the entire test volume with a minimal material expenditure (number of array elements and electronic channels).

The combined electronic and mechanical scanning of the test object allows a three-dimensional reconstruction of the test volume.

The utilization of the phased array makes it possible to test objects of arbitrarily complicated geometry. The surface contour can be reconstructed from the stored time signals, and the reconstruction of the test volume can be realized on the basis of the obtained profile information, namely with consideration of the laws of refraction.

LIST OF REFERENCE SYMBOLS

1 Workpiece
2 Ultrasonic transducer
3 Test region
4 Material discontinuity
5 Water bath

The invention claimed is:

1. A method for an imaging ultrasonic inspection of a three-dimensional workpiece, in which ultrasonic waves are coupled into the workpiece with at least one ultrasonic transducer and ultrasonic waves reflected within the workpiece are received by ultrasonic transducers and converted into ultrasonic signals forming a basis for non-destructive imaging ultrasonic inspection, comprising:
  a) n ultrasonic transducers disposed in a three-dimensional distribution positioned around a rod-shaped workpiece moving along a production line and a first ultrasonic transducer or a first group i of ultrasonic transducers is or are activated to provide acoustic irradiation of a first ultrasonic field or i ultrasonic fields into the workpiece without contact or via a coupling medium, wherein i<n;
  b) receiving ultrasonic waves reflected within the workpiece with m ultrasonic transducers provided in a three-dimensional distribution around the workpiece and generating m ultrasonic time signals containing amplitude information in a temporally resolved fashion;
  c) storing the m ultrasonic time signals;
  d) activating another ultrasonic transducer or another group i of ultrasonic transducers differing from the first group by at least one ultrasonic transducer and carrying out steps b) and c), wherein activation, reception and storage occur in one cycle;
  e) carrying out step d) repeatedly, wherein another ultrasonic transducer or another group of i ultrasonic transducers is selected, so that the another ultrasonic transducer or the another group of i ultrasonic transducers differs from an already selected ultrasonic transducer or from an already selected group of i ultrasonic transducers;
  f) reconstructing volumetric images, B-images and/or A-images by utilizing the stored ultrasonic time signals that are recorded in a sequence of cycles and stored; and wherein
  g) a sum of the ultrasonic time signals represents the acoustic irradiation of the workpiece by all n ultrasonic transducers.

2. The method according to claim 1, wherein:
receiving ultrasonic waves reflected within the workpiece with m of ultrasonic transducers disposed around the workpiece in a linear spatial distribution and partially overlapping in pairs reception apertures of the m ultrasonic transducer in the linear spatial distribution between two adjacently arranged ultrasonic transducers.

3. The method according to claim 1, wherein:
the acoustic irradiation of the ultrasonic field or the i ultrasonic fields is cyclic, and the acoustic irradiation takes place from a different direction in space for each cycle.

4. The method according to claim 2, wherein:
the acoustic irradiation of the ultrasonic field or the i ultrasonic fields is cyclic, and the acoustic irradiation takes place from a different direction in space for each cycle.

5. The method according to claim 3, wherein:
a difference between directions in space, from which an acoustic irradiation of the workpiece takes place per cycle, is as large as possible between two successive acoustic irradiations.

6. The method according to claim 4, wherein:
a difference between directions in space, from which an acoustic irradiation of the workpiece takes place per cycle, is as large as possible between two successive acoustic irradiations.

7. The method according to claim 1, wherein:
providing the n ultrasonic transducers in a uniform spatial distribution around the workpiece in a linear arrangement.

8. The method according to claim 2, wherein:
providing the n ultrasonic transducers in a uniform spatial distribution around the workpiece in a linear arrangement.

9. The method according to claim 3, wherein:
providing the n ultrasonic transducers in a uniform spatial distribution around the workpiece in a linear arrangement.

10. The method according to claim 4, wherein:
providing the n ultrasonic transducers in a uniform spatial distribution around the workpiece in a linear arrangement.

11. The method according to claim 5, wherein:
providing the n ultrasonic transducers in a uniform spatial distribution around the workpiece in a linear arrangement.

12. The method according to claim 6, wherein:
providing the n ultrasonic transducers in a uniform spatial distribution around the workpiece in a linear arrangement.

13. The method according to claim 1, wherein:
carrying out the cyclic acoustic irradiation of the ultrasonic fields into the workpiece from no more than n ultrasonic transducers within a time period, in which the workpiece moving in the longitudinal direction is quasi stationary.

14. The method according to claim 2, wherein:
carrying out the cyclic acoustic irradiation of the ultrasonic fields into the workpiece from no more than n ultrasonic transducers within a time period, in which the workpiece moving in the longitudinal direction is quasi stationary.

15. The method according to claim 3, wherein:
carrying out the cyclic acoustic irradiation of the ultrasonic fields into the workpiece from no more than n ultrasonic transducers within a time period, in which the workpiece moving in the longitudinal direction is quasi stationary.

16. The method according to claim 4, wherein:
carrying out the cyclic acoustic irradiation of the ultrasonic fields into the workpiece from no more than n ultrasonic transducers within a time period, in which the workpiece moving in the longitudinal direction is quasi stationary.

17. The method according to claim 5, wherein:
carrying out the cyclic acoustic irradiation of the ultrasonic fields into the workpiece from no more than n ultrasonic transducers within a time period, in which the workpiece moving in the longitudinal direction is quasi stationary.

18. The method according to claim 1, wherein:
arranging the n ultrasonic transducers in a linear arrangement, in which the ultrasonic transducers are spaced apart from one another by a distance that is greater than half the ultrasonic wavelength.

19. The method according to claim 2, wherein:
arranging the n ultrasonic transducers in a linear arrangement, in which the ultrasonic transducers are spaced apart from one another by a distance that is greater than half the ultrasonic wavelength.

20. The method according to claim 3, wherein:
arranging the n ultrasonic transducers in a linear arrangement, in which the ultrasonic transducers are spaced apart from one another by a distance that is greater than half the ultrasonic wavelength.

21. The method according to claim 4, wherein:
arranging the n ultrasonic transducers in a linear arrangement, in which the ultrasonic transducers are spaced apart from one another by a distance that is greater than half the ultrasonic wavelength.

22. The method according to claim 5, wherein:
arranging the n ultrasonic transducers in a linear arrangement, in which the ultrasonic transducers are spaced apart from one another by a distance that is greater than half the ultrasonic wavelength.

23. The method according to claim 6, wherein:
arranging the n ultrasonic transducers in a linear arrangement, in which the ultrasonic transducers are spaced apart from one another by a distance that is greater than half the ultrasonic wavelength.

24. The method according to claim 1, wherein:
providing the ultrasonic irradiation with immersion technology.

25. The method according to claim 1, wherein:
the ultrasonic transducers transmit and receive ultrasonic waves, and n=m.

26. The method according to claim 1, wherein:
B-images are produced and assembled in layers to obtain a volumetric image.

* * * * *